United States Patent
Chen

(10) Patent No.: US 10,345,248 B2
(45) Date of Patent: Jul. 9, 2019

(54) OPTICAL SYSTEM AND METHOD FOR INSPECTING A TRANSPARENT PLATE

(71) Applicant: STEK CO., LTD, Taichung (TW)

(72) Inventor: Ming-Sheng Chen, Taichung (TW)

(73) Assignee: STEK CO. LTD, Taichung (TW)

( * ) Notice: Subject to any disclaimer, the term of this patent is extended or adjusted under 35 U.S.C. 154(b) by 0 days.

(21) Appl. No.: 15/697,083

(22) Filed: Sep. 6, 2017

(65) Prior Publication Data

US 2018/0238813 A1   Aug. 23, 2018

(30) Foreign Application Priority Data

Feb. 17, 2017   (TW) .............................. 106105196 A

(51) Int. Cl.
| | |
|---|---|
| *G01N 21/94* | (2006.01) |
| *G01N 21/89* | (2006.01) |
| *G01N 21/896* | (2006.01) |
| *G01N 21/88* | (2006.01) |

(52) U.S. Cl.
CPC ......... *G01N 21/94* (2013.01); *G01N 21/8806* (2013.01); *G01N 21/8901* (2013.01); *G01N 21/896* (2013.01)

(58) Field of Classification Search
CPC .... G01N 21/47; G01N 21/94; G01N 21/8806; G01N 21/8901; G01N 21/896; G01B 9/02
See application file for complete search history.

(56) References Cited

U.S. PATENT DOCUMENTS

| | | | | |
|---|---|---|---|---|
| 5,917,590 | A | * | 6/1999 | Greve ................ G01N 21/8806 250/559.48 |
| 2005/0219546 | A1 | * | 10/2005 | Otsuka ............... G01D 5/34715 356/499 |

* cited by examiner

*Primary Examiner* — Jamil Ahmed

(57) ABSTRACT

An optical system for inspecting a transparent plate includes a light source for casting incident light onto a face of the transparent plate so that there is a primary reflected light and secondary reflected light from the face of the transparent plate, a photo sensor for receiving light from the face of the transparent plate, and a blocking element for blocking the secondary reflected light while allowing the primary reflected light to reach the photo sensor.

6 Claims, 3 Drawing Sheets

OPTICAL SYSTEM AND METHOD FOR INSPECTING A TRANSPARENT PLATE

BACKGROUND OF INVENTION

1. Field of Invention

The present invention relates to optical inspection of a transparent plate and, more particularly, to an optical system and method for detecting a stain on a face of a transparent plate.

2. Related Prior Art

Referring to FIG. 1, a conventional mask-inspecting apparatus includes a light source L and a photo sensor C such as a charge-coupled device ("CCD") or a complementary metal-oxide semiconductor ("CMOS"). The light source L casts light (the "incident light") Lo onto a face P1 of a transparent plate P. The face P1 reflects the incident light Lo and transmits reflected light Lr (the "primary reflected light Lr1") to the photo sensor C. There are an incident angle $\theta 1$ between the incident light Lo and a normal line of the face P1 and a reflection angle $\theta 2$ between the primary reflected light Lr1 and the normal line of the face P1. The incident angle $\theta 1$ is identical to the reflection angle $\theta 2$. The photo sensor C receives and processes the primary reflected light Lr1 from the face P1 to detect any stain on the face P1.

However, according to Snell's Law, some of the incident light Lo (the "light Lc") goes through the face P1 and gets refracted, and then reaches another face P2 of the transparent plate P. Some of the light Lc gets reflected from the face P2. Some of the light reflected from the face P2 gets refracted by the face P1 and becomes secondary reflected light Lr2. Such a process continues until the light is too weak to be detected by the photo sensor C.

Referring to FIG. 2, there are superimposed images because the photo sensor C receives the secondary reflected light Lr2 or any other light reflected from the face P2 and refracted by the face P1 in addition to the primary reflected light Lr1. For example, there is a stain A on the face P1, and there is a stain B on the face P2. The photo sensor C detects both of the stains A and B. Hence, the stain A on the face P1 cannot be detected effectively. In addition, it is difficult to determine the focal length since the plate P is a transparent element without any reference point, and this further reduces the efficiency of the inspection.

To overcome the above-mentioned problem, there has been an attempt to enlarge the scanned range and delete the superimposed images by providing a linear light source to cast light onto the transparent plate P, with the incident angle $\theta 1$ set to be about 85 degrees, i.e., the incident light Lo is close to the face P1. This approach keeps the photo sensor C from any secondary reflected light. However, the shadow of a stain is longer as the incident angle $\theta 1$ is smaller, and a long shadow renders it difficult to determine the size of the stain. Moreover, it is difficult for the incident light to produce an image of a planar stain such as atomization, grease or fingerprint if the incident angle is small.

To solve the foregoing problem, there has been an attempt to provide the mask-inspecting apparatus with two light sources. This approach solves the problem of misjudging of the size of a stain. However, this inevitably increases the cost of the mask-inspecting apparatus.

The present invention is therefore intended to obviate or at least alleviate the problems encountered in prior art.

SUMMARY OF INVENTION

It is an objective of the present invention to provide a method for inspecting a transparent plate that includes two faces.

To achieve the foregoing objective, the optical method includes the step of providing a light source and a photo sensor near the first face of the transparent plate. The light source casts incident light onto the first face of the transparent plate. The photo sensor receives light from the first face of the transparent plate. A grating is located between the first face of the transparent plate and both of the light source and the photo sensor. The grating includes an incident passageway and a reflection passageway. The incident light reaches the first face of the transparent plate through the incident passageway. Only primary reflected light from the first face of the transparent plate reaches the photo sensor through the reflection passageway while secondary reflected light and any other light reflected from the second face of the transparent plate and refracted by the first face of the transparent plate is blocked by the grating. Then, the transparent plate is moved relative to the light source, the photo sensor and the grating, thereby scanning the entire first face to determine whether there is any stain on the first face.

It is another objective of the present invention to provide an optical system for inspecting a transparent plate that includes two faces.

To achieve the foregoing objective, the optical system includes a light source for casting light onto the first face of the transparent plate, a photo sensor for receiving light from the first face of the transparent plate, a grating for blocking some of the light from the first face of the transparent plate. The photo sensor continuously scans regions of the first face of the transparent plate when the transparent plate is moved relative to the light source, the photo sensor and the grating. The light source and the photo sensor are located on a side of the grating while the transparent plate is located on another side of the grating. The grating includes an incident passageway and a reflection passageway. The incident light reaches the first face of the transparent plate through the incident passageway. Only primary reflected light from the first face of the transparent plate reaches the photo sensor through the reflection passageway while secondary reflected light and any other light reflected from the second face of the transparent plate and refracted by the first face of the transparent plate is blocked by the grating.

Other objectives, advantages and features of the present invention will be apparent from the following description referring to the attached drawings.

BRIEF DESCRIPTION OF DRAWINGS

The present invention will be described via detailed illustration of the preferred embodiment in view of the prior art referring to the drawings wherein.

DETAILED DESCRIPTION OF PREFERRED EMBODIMENT

Figure 1:
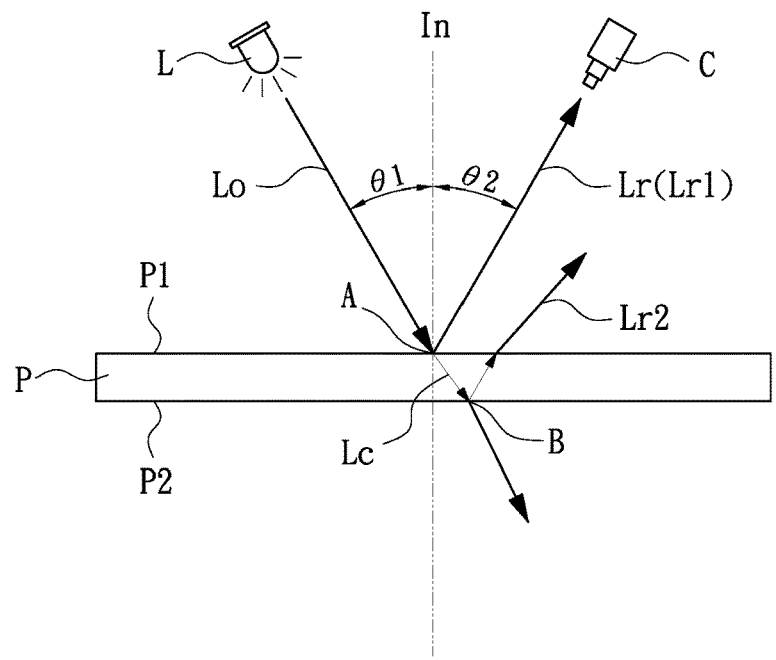
FIG. 1 is a front view of a conventional mask-inspecting apparatus.
Figure 2:
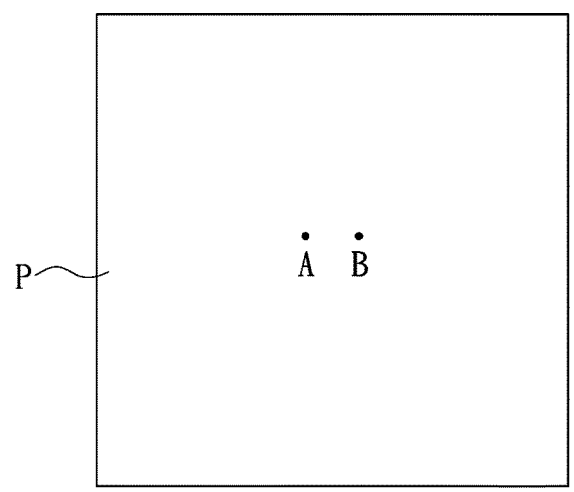
FIG. 2 is an image of a transparent plate obtained by the conventional mask-inspecting apparatus shown in FIG. 1.
Figure 3:
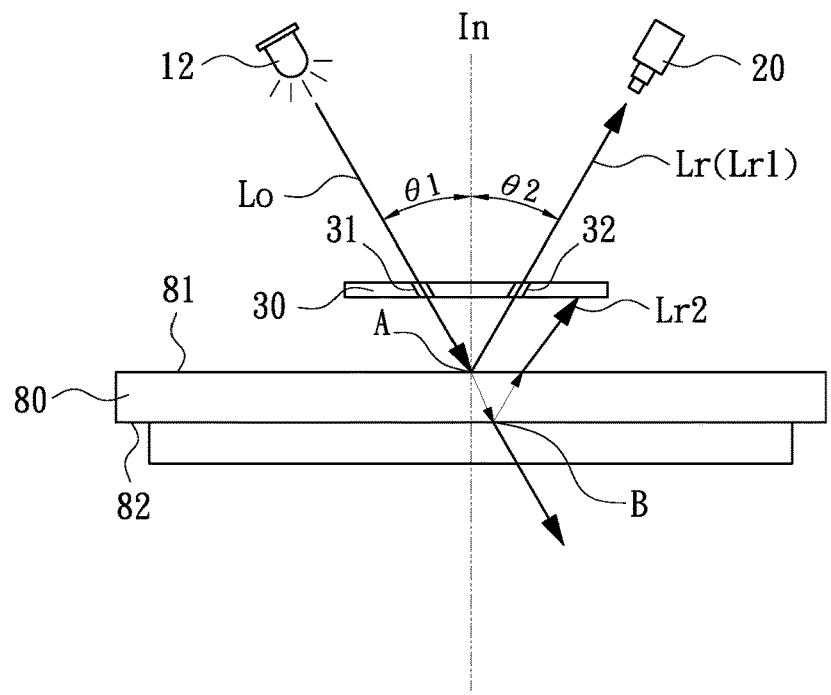
FIG. 3 is a front view of an optical system for inspecting a transparent plate according to the preferred embodiment of the present invention.

Referring to FIG. 3, to inspect a transparent plate 80 for use in a semiconductor product, a panel or a package, there is provided an optical system that includes a light source 10, a photo sensor 20 and a grating 30 according to the preferred embodiment of the present invention. The transparent plate 80 includes a first face 81 and a second face 82. The light source 10 can be a halogen lamp, and LED lamp, a high-frequency fluorescent lamp, a metal lamp, a xenon lamp or a laser lamp that emits visible or invisible light. The photo sensor 20 can be a charge-coupled device ("CCD") or a complementary metal-oxide semiconductor ("CMOS") element. The grating 30 blocks light.

The light source 10 and the photo sensor 20 are located on a side of the first face 81 of the transparent plate 80. The light source 10 and the photo sensor 20 are located on two different sides of a normal line In of the first face 81.

The grating 30 is arranged so that the light source 10 and the photo sensor 20 are on a side of the grating 30 while the transparent plate 80 is on another side of the grating 30. The grating 30 includes an incident passageway 31 and a reflection passageway 32 at identical distances from the normal line In.

The light source 10 casts incident light Lo onto the first face 81 of the transparent plate 80. The first face 81 of the transparent plate 80 reflects the incident light Lo and hence sends primary reflected light Lr1 to the photo sensor 20. The incident angle $\theta 1$ of the incident light Lo is identical to the reflection angle $\theta 2$ of the primary reflected light Lr1. The incident angle $\theta 1$ is preferably 15 to 45 degrees. More preferably, the incident angle $\theta 1$ is 27 to 33 degrees.

The width of the incident passageway 31 is preferably 0.1 to 0.5 mm. The width of the reflection passageway 32 is smaller than the distance between the primary reflected light Lr1 and secondary reflected light Lr2 from the second face 82 of the transparent plate 80. Thus, the second face reflected light Lr2 and any other light reflected from the second face 82 and refracted by the first face 81 is blocked by the grating 30 when the primary reflected light Lr1 goes through the reflection passageway 32. Thus, the photo sensor 20 does not receive the secondary reflected light Lr2 and any other light reflected from the second face 82 and refracted by the first face 81. The width of the reflection passageway 32 is preferably 0.2 to 20 mm.

Thus, the incident light Lo cast onto the transparent plate 80 from the light source 10 is limited to a certain angle, thereby allowing the primary reflected light Lr1 from transparent plate 80 to reach the photo sensor 20, but keeping the photo sensor 20 from the secondary reflected light Lr2.

Figure 4:
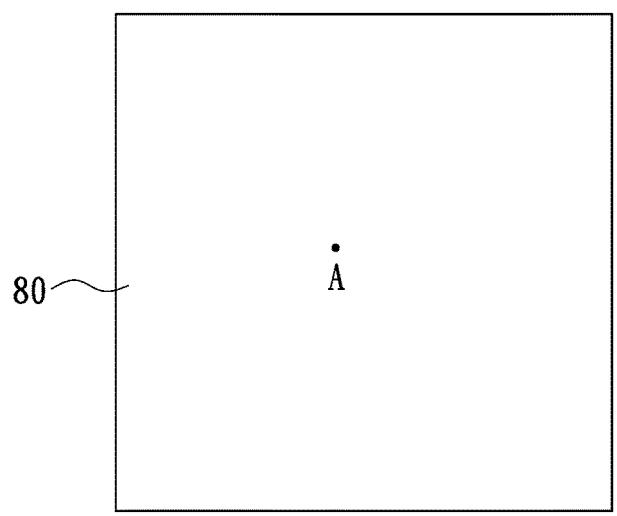
FIG. 4 is an image of a transparent plate obtained by the optical system shown in FIG. 3.

Referring to FIG. 4, there is a stain A on the first face 81, and there is a stain B on the second face 82. However, the photo sensor 20 receives only the primary reflected light Lr1 and provides an image of the stain A, but does not receive the secondary reflected light Lr2 or provide an image of the stain B.

Figure 5:
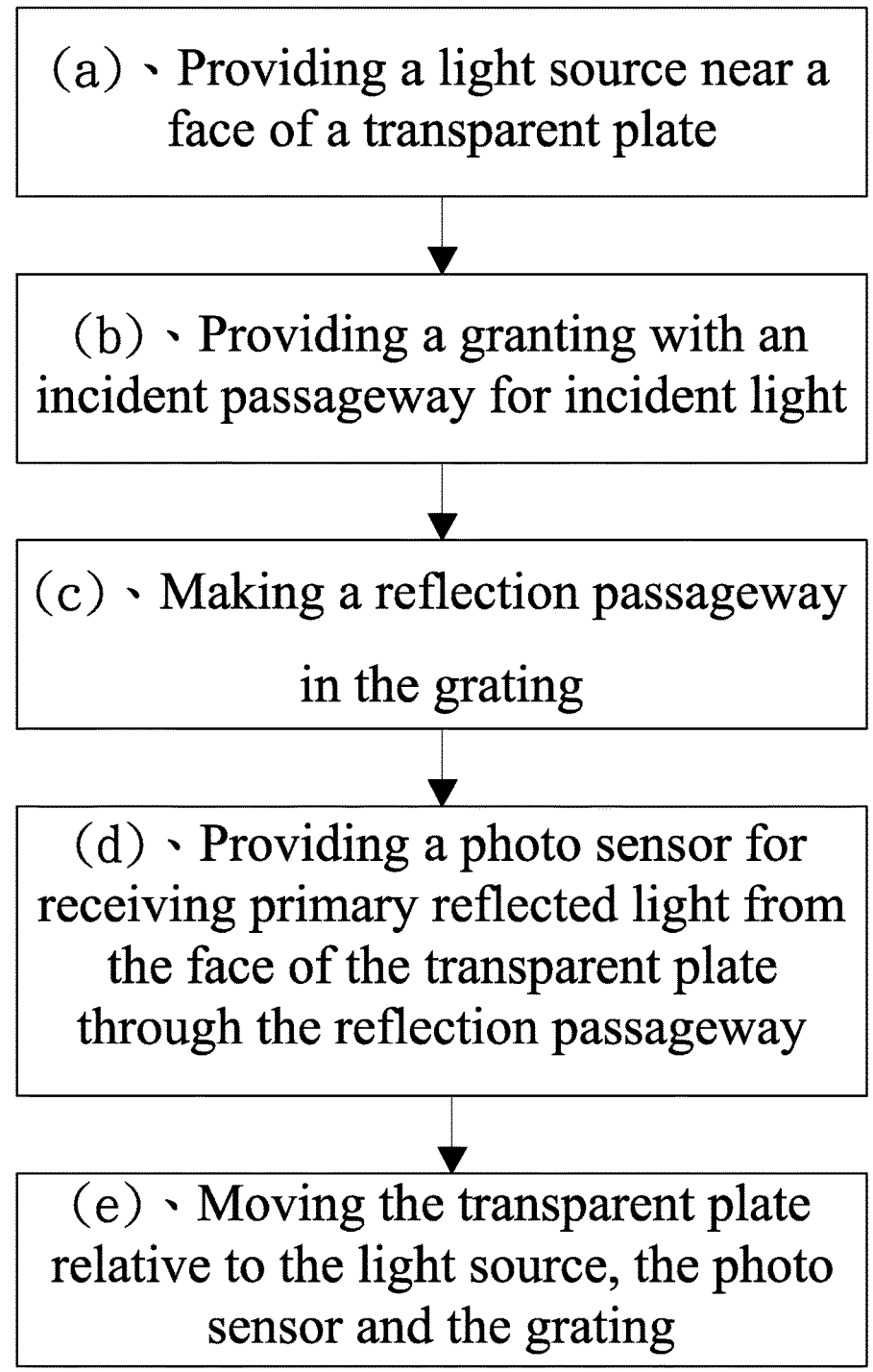
FIG. 5 is a flow chart of an optical method executed in the optical system shown in FIG. 3.

Referring to FIG. 5, an optical method is executed to inspect a transparent plate 80. The thickness of the transparent plate 80 is the distance between two faces 81 and 82.

At (a), a light source 10 is located near the first face 81 of the transparent plate 80 for example. The light source 10 cast light onto the first face 81.

At (b), an incident passageway 31 is made in a granting 30 that located between the light source 10 and the transparent plate 80. The width of the incident passageway 31 is preferably 0.1 to 0.5 mm. The light source 10 casts incident light Lo onto the first face 81 of the transparent plate 80 through the incident passageway 31. There is an incident angle $\theta 1$ between the incident light Lo and the normal line of the first face 81. The incident angle $\theta 1$ is preferably 15 to 45 degrees and, more particularly, 27 to 33 degrees. The first face 81 of the transparent plate 80 reflects some of the incident light Lo and hence provides primary reflected light Lr1.

At (c), the grating 30 is made with a reflection passageway 32. The reflection passageway 32 and the incident passageway 31 are located on two different sides the normal line of the first face 81. The primary reflected light Lr1 reaches the second face 82 of the transparent plate 80 through the reflection passageway 32. The width of the reflection passageway 32 is smaller than the distance between the primary reflected light Lr1 and the secondary reflected light Lr2. Thus, the second face reflected light Lr2 and any other light after the secondary reflected light Lr2 is blocked by the grating 30 when the primary reflected light Lr1 goes through the reflection passageway 32. Thus, the photo sensor 20 does not receive the secondary reflected light Lr2 and any other light after the secondary reflected light Lr2. The width of the reflection passageway 32 is preferably 0.2 to 20 mm.

At (d), there is provided a photo sensor 20 for receiving the primary reflected light Lr1 from the first face 81 through the reflection passageway 32. The photo sensor 20 is located near the first face 81 of the transparent plate 80. The photo sensor 20 and the light source 10 are located on different sides of the normal line In of the first face 81 of the transparent plate 80. The photo sensor 20 receives the primary reflected light Lr1 from the first face 81 of transparent plate 80 through the reflection passageway 32 of the grating 30. The photo sensor 20 does not receive the secondary reflected light Lr2 or any other light reflected from the second face 82 and refracted by the first face 81, which is blocked by the grating 30

At (e), the transparent plate 80 is moved relative to the light source 10, the photo sensor 20 and the grating 30 to provide an image of the entire first face 81 of the transparent plate 80 to determine whether there is any stain on the first face 81 of the transparent plate 80. The transparent plate 80 is moved in a direction perpendicular to the normal line In while the light source 10, the photo sensor 20 and the grating 30 are kept in position and in operation. Thus, the photo sensor 20 continuously receives the primary reflected light Lr1 from all regions in the first face 81 of the transparent plate 80. The photo sensor 20 converts the primary reflected light Lr1 into charge. The stronger the primary reflected light Lr1 is, the larger the charge is. The charge is used to determine the intensity of the primary reflected light Lr1. Therefore, the primary reflected light Lr1 from a region of the first face 81 will be relatively weak if there is a stain on that region in the first face 81. Thus, the photo sensor 20 continuously receives the primary reflected light Lr1 from all of the regions in the first place 81 of the transparent plate 80 and accordingly provides an image of the entire first face 81 of the transparent plate 80. Thus, the size, shape and type of any stain on the first face 81 of the transparent plate 80 can be determined.

As discussed above, the grating 30 blocks the second reflected light Lr2 and any other light reflected from the second face 82 and refracted by the first face 81. Hence, only the primary reflected light Lr1, which is reflected from the first face 81 of the transparent plate 80, reaches the photo sensor 20. Thus, the image of the first face 81 is not interfered with any image of the second face 82. Accordingly, the optical system of the present invention precisely and effectively determines the size, shape and type of any stain on the first face 81 of the transparent plate 80, even atomization, grease or fingerprint.

Moreover, the photo sensor 20 only receives the primary reflected light Lr1 from the first face 81 of the transparent plate 80 that is expected to be inspected, the reflected light is specific, and the focusing is fast, and the inspection is efficient. At the same time, an ordinary light source can be used in the optical system of the present invention, and the cost of the optical system is hence low.

The present invention has been described via the illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. An optical method for inspecting a transparent plate that includes a first face to be inspected and a second face, the optical method comprising the steps of:
    providing a light source near the first face of the transparent plate, wherein the light source casts incident light onto the first face of the transparent plate at an incident angle of 27 to 33 degrees;
    providing a photo sensor near the first face of the transparent plate, wherein the photo sensor receives light from the first face of the transparent plate;
    providing a grating between the first face of the transparent plate and both of the light source and the photo sensor, wherein the grating comprises an incident passageway and a reflection passageway, wherein the incident light reaches the first face of the transparent plate through the incident passageway, wherein only primary reflected light from the first face of the transparent plate reaches the photo sensor through the reflection passageway while secondary reflected light and any other light reflected from the second face of the transparent plate and refracted by the first face of the transparent plate is blocked by the grating, wherein the reflection passageway is made with width smaller than distance between the primary reflected light and the secondary reflected light; and
    moving the transparent plate relative to the light source, the photo sensor and the grating, thereby scanning the entire first face to determine whether there is any stain on the first face.

2. The optical method according to claim 1, wherein the incident passageway is made with width of 0.1 to 0.5 mm.

3. The optical method according to claim 1, wherein the width of the reflection passageway is 0.2 to 20 mm.

4. An optical system for inspecting a transparent plate that includes a first face to be inspected and a second face, the optical system comprises a light source for casting light onto the first face of the transparent plate at an incident angle of 27 to 33 degrees, a photo sensor for receiving light from the first face of the transparent plate, a grating for blocking some of the light from the first face of the transparent plate;
    wherein the photo sensor continuously scans regions of the first face of the transparent plate when the transparent plate is moved relative to the light source, the photo sensor and the grating;
    wherein the light source and the photo sensor are located on a side of the grating while the transparent plate is located on another side of the grating;
    wherein the grating comprises an incident passageway and a reflection passageway, wherein the incident light reaches the first face of the transparent plate through the incident passageway, wherein only primary reflected light from the first face of the transparent plate reaches the photo sensor through the reflection passageway while secondary reflected light and any other light reflected from the second face of the transparent plate and refracted by the first face of the transparent plate is blocked by the grating, wherein the reflection passageway is made with width smaller than distance between the primary reflected light and the secondary reflected light.

5. The optical system according to claim 4, wherein the incident passageway is made with width of 0.1 to 0.5 mm.

6. The optical system according to claim 4, wherein the width of the reflection passageway is 0.2 to 20 mm.

* * * * *